US 9,976,971 B2

(12) United States Patent
Cernatescu et al.

(10) Patent No.: US 9,976,971 B2
(45) Date of Patent: May 22, 2018

(54) SYSTEMS AND METHODS FOR X-RAY DIFFRACTION

(71) Applicant: UNITED TECHNOLOGIES CORPORATION, Farmington, CT (US)

(72) Inventors: Iuliana Cernatescu, Glastonbury, CT (US); David U. Furrer, Marlborough, CT (US)

(73) Assignee: UNITED TECHNOLOGIES CORPORATION, Farmington, CT (US)

(*) Notice: Subject to any disclaimer, the term of this patent is extended or adjusted under 35 U.S.C. 154(b) by 401 days.

(21) Appl. No.: 14/639,460

(22) Filed: Mar. 5, 2015

(65) Prior Publication Data

US 2015/0253262 A1 Sep. 10, 2015

Related U.S. Application Data

(60) Provisional application No. 61/948,806, filed on Mar. 6, 2014.

(51) Int. Cl.
*G01N 23/20* (2018.01)
*G01N 23/207* (2018.01)
(Continued)

(52) U.S. Cl.
CPC ....... *G01N 23/20008* (2013.01); *G01N 23/20* (2013.01); *G01N 23/207* (2013.01);
(Continued)

(58) Field of Classification Search
CPC .......... H01J 35/02; H01J 35/025; H01J 35/08; H01J 35/10; H01J 35/101; H01J 35/16;
(Continued)

(56) References Cited

U.S. PATENT DOCUMENTS 4,259,580 A * 3/1981 Vogler ............... H05G 1/58
378/94
4,712,226 A * 12/1987 Horbaschek ......... H01J 35/06
378/124

(Continued)

FOREIGN PATENT DOCUMENTS

EP 0118932 A1 9/1984
EP 2248552 A1 11/2010
(Continued)

OTHER PUBLICATIONS

Liu C., et al., "Origin and Development of Residual Stresses in the Ni—NiO System: in-situ Studies at High Temperature by X-ray Diffraction", Materials Science and Engineering A: Structural Materials: Properties, Microstructures and Processing, Elsevier BV, NL, vol. 160, No. 1, Jan. 15, 1993) pp. 113-126.
(Continued)

*Primary Examiner* — Allen C. Ho
(74) *Attorney, Agent, or Firm* — Cantor Colburn LLP (57) ABSTRACT

An x-ray diffraction system includes an x-ray source having a first interchangeable x-ray generating component, a second interchangeable x-ray generating component, an actuator and a controller operatively connected to the actuator. The first and second interchangeable x-ray generating components are interchangeable with one another. The actuator is operatively connected to the first and second interchangeable x-ray generating components. A method for non-destructive x-ray diffraction includes emitting a first x-ray beam from an x-ray source with a first interchangeable x-ray generating component based on a first desired depth to measure a crystallographic signature of a sample at the first desired depth, interchanging the first interchangeable x-ray generating component with a second interchangeable x-ray generating component to form a modified x-ray source, and emitting a second x-ray beam from the modified x-ray
(Continued)

source based on a second desired depth, to non-destructively measure a crystallographic signature of the sample at the second desired depth.

11 Claims, 5 Drawing Sheets (51) Int. Cl.
H01J 35/02 (2006.01)
H01J 35/10 (2006.01)
H01J 35/16 (2006.01)
H01J 35/08 (2006.01)
H01J 35/24 (2006.01)
H01J 35/26 (2006.01)

(52) U.S. Cl.
CPC ........ G01N 23/20025 (2013.01); H01J 35/02 (2013.01); H01J 35/025 (2013.01); H01J 35/08 (2013.01); H01J 35/10 (2013.01); H01J 35/101 (2013.01); H01J 35/16 (2013.01); H01J 35/24 (2013.01); H01J 35/26 (2013.01); H01J 2235/081 (2013.01); H01J 2235/086 (2013.01)

(58) Field of Classification Search
CPC ...... H01J 35/24; H01J 35/26; H01J 2235/081; H01J 2235/086; G01N 23/20; G01N 23/20008; G01N 23/20025; G01N 23/207
USPC ........ 378/9, 44–50, 71, 73, 79, 81, 92, 98.9, 378/98.11, 114–118, 121, 124, 143, 144
See application file for complete search history.

(56) References Cited

U.S. PATENT DOCUMENTS

| | | | | |
|---|---|---|---|---|
| 5,142,652 A * | 8/1992 | Reichenberger | H01J 35/06 378/125 |
| 5,383,232 A * | 1/1995 | Gabbay | H01J 35/10 378/124 |
| 5,490,196 A * | 2/1996 | Rudich | G01V 5/0041 378/101 |
| 5,511,105 A * | 4/1996 | Knott | H01J 35/24 378/125 |
| 5,907,592 A * | 5/1999 | Levinson | H01J 35/10 378/144 |
| 6,125,167 A * | 9/2000 | Morgan | H01J 35/10 378/121 |
| 6,154,521 A * | 11/2000 | Campbell | H01J 35/12 378/125 |
| 6,212,257 B1 * | 4/2001 | Mattern | H01J 35/24 378/125 |
| 6,229,870 B1 * | 5/2001 | Morgan | A61B 6/032 378/4 |
| 6,301,330 B1 * | 10/2001 | Kurtz | G01N 23/20 257/E21.53 |
| 6,487,274 B2 * | 11/2002 | Bertsche | A61N 5/10 378/124 |
| 6,560,315 B1 * | 5/2003 | Price | H01J 35/10 378/125 |
| 6,914,959 B2 * | 7/2005 | Bailey | A61B 6/022 378/41 |
| 6,983,035 B2 * | 1/2006 | Price | H01J 35/08 378/124 |
| 7,003,077 B2 * | 2/2006 | Jen | A61B 6/032 378/124 |
| 7,035,371 B2 * | 4/2006 | Boese | A61B 6/022 378/41 |
| 7,035,373 B2 * | 4/2006 | Omote | G21K 1/06 378/71 |
| 7,065,179 B2 * | 6/2006 | Block | H01J 35/10 378/124 |
| 7,103,137 B2 * | 9/2006 | Seppi | G01N 23/04 378/57 |
| 7,103,138 B2 * | 9/2006 | Pelc | A61B 6/032 378/4 |
| 7,120,222 B2 * | 10/2006 | Hoffman | A61B 6/032 378/124 |
| 7,158,609 B2 * | 1/2007 | Kikuchi | G01N 23/205 378/70 |
| 7,184,514 B2 * | 2/2007 | Kudo | H01J 35/10 378/144 |
| 7,187,756 B2 * | 3/2007 | Gohno | G01N 23/046 378/124 |
| 7,206,373 B2 * | 4/2007 | Seufert | A61B 6/032 378/4 |
| 7,242,745 B2 * | 7/2007 | He | G01N 23/20016 378/81 |
| 7,257,192 B2 * | 8/2007 | Omote | G01N 23/201 378/81 |
| 7,258,485 B2 * | 8/2007 | Nakano | G01N 23/20016 378/196 |
| 7,269,245 B2 * | 9/2007 | He | G01N 23/20016 356/301 |
| 7,305,063 B2 * | 12/2007 | Heuscher | H01J 35/101 378/12 |
| 7,317,784 B2 * | 1/2008 | Durst | G01N 23/20 378/124 |
| 7,551,722 B2 * | 6/2009 | Ohshima | G01N 23/04 378/143 |
| 7,606,349 B2 * | 10/2009 | Oreper | G01V 5/0025 378/137 |
| 7,616,731 B2 * | 11/2009 | Pack | G01N 23/046 378/10 |
| 7,649,981 B2 * | 1/2010 | Seppi | A61B 6/032 378/124 |
| 7,706,499 B2 * | 4/2010 | Pack | G01T 1/2985 378/10 |
| 7,809,101 B2 * | 10/2010 | Frutschy | H01J 35/06 378/124 |
| 7,809,113 B2 * | 10/2010 | Aoki | G01N 23/223 378/124 |
| 7,826,585 B2 * | 11/2010 | Proksa | A61B 6/032 378/5 |
| 7,826,594 B2 * | 11/2010 | Zou | H01J 1/30 378/10 |
| 7,835,486 B2 * | 11/2010 | Basu | G01T 1/2985 378/10 |
| 7,852,986 B2 * | 12/2010 | Loef | H05G 1/10 378/101 |
| 7,864,917 B2 * | 1/2011 | Ribbing | A61B 6/032 378/10 |
| 7,869,561 B2 * | 1/2011 | Dafni | A61B 6/032 378/19 |
| 7,869,571 B2 * | 1/2011 | Hsieh | A61B 6/032 378/124 |
| 7,869,862 B2 * | 1/2011 | Seppi | A61B 6/032 600/420 |
| 7,889,844 B2 * | 2/2011 | Okunuki | H01J 35/065 378/122 |
| 7,920,676 B2 * | 4/2011 | Yun | G01N 23/201 378/70 |
| 7,933,378 B2 * | 4/2011 | Proksa | A61B 6/032 378/9 |
| 7,949,089 B2 * | 5/2011 | Dafni | A61B 6/032 378/9 |
| 7,949,102 B2 * | 5/2011 | Behling | A61B 6/032 378/119 |
| 7,991,114 B2 * | 8/2011 | Okunuki | A61B 6/032 378/11 |
| 8,180,017 B2 * | 5/2012 | Forthmann | A61B 6/032 378/156 |
| 8,270,562 B2 * | 9/2012 | Sainath | A61B 6/4429 378/124 |
| 8,300,767 B1 * | 10/2012 | Matsushita | G01N 23/207 378/70 |
| 8,483,361 B2 * | 7/2013 | Sainath | A61B 6/027 378/125 |

(56) References Cited

U.S. PATENT DOCUMENTS

| | | | | |
|---|---|---|---|---|
| 8,537,965 | B2* | 9/2013 | Dafni | A61B 6/032 378/4 |
| 8,619,946 | B2* | 12/2013 | Hanke | H01J 35/10 378/124 |
| 8,687,766 | B2* | 4/2014 | Wormington | G01N 23/207 378/70 |
| 8,693,638 | B2* | 4/2014 | Dafni | A61B 6/032 378/124 |
| 8,699,657 | B2* | 4/2014 | Baeumer | A61B 6/032 250/494.1 |
| 8,848,864 | B2* | 9/2014 | Jeong | G01N 23/046 378/21 |
| 8,953,743 | B2* | 2/2015 | Yasukawa | G01L 1/25 378/72 |
| 9,177,755 | B2* | 11/2015 | Parker | H01J 35/10 |
| 9,198,629 | B2* | 12/2015 | Wiedmann | H01J 35/10 |
| 9,390,881 | B2* | 7/2016 | Yun | G21K 1/06 |
| 9,449,781 | B2* | 9/2016 | Yun | H01J 35/08 |
| 2007/0248215 | A1 | 10/2007 | Ohshima et al. | |
| 2014/0029726 | A1 | 1/2014 | Yasukawa | |

FOREIGN PATENT DOCUMENTS

| | | |
|---|---|---|
| EP | 2542035 A1 | 1/2013 |
| GB | 2133208 A | 7/1984 |

OTHER PUBLICATIONS

Gross, K. A., et al., "Oxyapatite in Hydroxyapatite Coatings", Journal of Materials Science, vol. 33, No. 15, Aug. 1, 1998, pp. 3985-3991.

Extented European Search Report dated Jun. 29, 2015, issued on corresponding European Patent Application No. 15157955.4-1559.

* cited by examiner

SYSTEMS AND METHODS FOR X-RAY DIFFRACTION

CROSS-REFERENCE TO RELATED APPLICATION

This application claims the benefit of priority under 35 U.S.C. § 119(e) to U.S. Provisional Application No. 61/948,806, filed Mar. 6, 2014, which is incorporated herein by reference in its entirety.

BACKGROUND OF THE INVENTION

1. Field of the Invention

The present invention relates to non-destructive residual stress assessments by X-ray diffraction and, in particular, to systems and methods for X-ray diffraction measurements to evaluate the crystallographic signature of crystalline materials.

2. Description of Related Art

Traditional x-ray diffraction systems are used to measure crystallographic signatures of crystalline materials, e.g. materials used to manufacture aerospace components. These crystallographic signatures can be used to evaluate parameters, such as, residual stress and strain, texture, phase type and composition, unit-cell variation, shear stresses, dislocation density, and the like. Generally, x-ray diffraction can be applied as a non-destructive, near-surface characterization method. To obtain measurements at different depths, e.g. below-surface, traditional x-ray diffraction systems require layer removal by machining or etching of the surface layer of the sample being tested, which can be permanently destructive to the sample.

Such conventional methods and systems have generally been considered satisfactory for their intended purpose. However, there is still a need in the art for systems and methods that allow for both non-destructive near-surface and non-destructive below-surface measurements. The present invention provides a solution for these problems.

SUMMARY OF THE INVENTION

An x-ray diffraction system includes an x-ray source having a first interchangeable x-ray generating component, a second interchangeable x-ray generating component, an actuator and a controller operatively connected to the actuator. The second interchangeable x-ray generating component is interchangeable with the first interchangeable x-ray generating component. The actuator is operatively connected to the first and second interchangeable x-ray generating components for mechanically interchanging the first interchangeable x-ray generating component with the second interchangeable x-ray generating component.

In accordance with one aspect of the invention, the x-ray diffraction system can include a carousel. The first and second interchangeable x-ray generating components can be mounted to the carousel. The carousel can be a linear carousel, and/or a rotary carousel. The actuator can be operatively connected to the carousel for movement thereof to mechanically interchange the first and second interchangeable x-ray generating components. The x-ray diffraction system can include a shaft defining a shaft axis. The rotary carousel can be operatively connected to the shaft. The actuator can be operatively connected to the shaft to drive rotation of the shaft and the rotary carousel about the shaft axis for mechanically interchanging the first and second interchangeable x-ray generating components.

In accordance with another aspect of the invention, the first and second interchangeable x-ray generating components can be first and second interchangeable x-ray targets. The system can further include an x-ray tube. The first and second interchangeable x-ray targets can be disposed within the x-ray tube. The first interchangeable x-ray target can be configured to emit a first x-ray beam at a first energy and first wavelength, while the second interchangeable x-ray target can be configured to emit a second x-ray beam at a second energy and second wavelength. The first energy and/or the first wavelength can be different from the second energy and/or second wavelength, respectively. The first and/or the second interchangeable x-ray targets can include copper, silver, chromium, vanadium, manganese, cobalt, molybdenum, and/or titanium.

In certain embodiments, the first and second interchangeable x-ray generating components can also be first and second interchangeable x-ray tubes. The first interchangeable x-ray tube can be configured to emit a first x-ray beam at a first energy and first wavelength, while the second interchangeable x-ray tube can be configured to emit a respective second x-ray beam at a second energy and second wavelength, wherein the first energy and/or the first wavelength can be different from the second energy and/or the second wavelength, respectively. The first interchangeable x-ray tube and the second interchangeable x-ray tube can each include a respective x-ray target. The x-ray target of the first interchangeable x-ray tube can be different from the x-ray target of the second interchangeable x-ray tube.

It is also contemplated that the system can include a multi-axis sample stage operatively connected to the controller. The controller can be configured to adjust the alignment of the sample stage relative to the x-ray source to adjust an angle of incidence between an x-ray emitted by the x-ray source and a sample on the sample stage. The controller can be configured to adjust the alignment of the multi-axis sample stage based on a desired crystallographic measurement depth in the sample. The controller can also be configured to direct the actuator to interchange the first interchangeable x-ray generating component with the second interchangeable x-ray generating component based on a desired crystallographic measurement depth in a sample for a second non-destructive below surface measurement.

In accordance with certain embodiments, a tangible, non-transitory, computer-readable media (e.g., disks/CDs/RAM/EEPROM/etc.) has software encoded thereon. The software, when executed by a processor, is operative to receive a desired crystallographic measurement depth of a sample, and to select at least one of an x-ray target, incident beam collimating optic and diffracted beam collimating optic for use in non-destructive x-ray crystallography to achieve the desired crystallographic measurement depth of the sample.

The software, when executed by a processor, is further operative to execute a command to cause an actuator to mechanically alter at least one of a current x-ray target, incident beam collimating optic and diffracted beam collimating optic to match the selected x-ray target, incident beam collimating optic and diffracted beam collimating optic for non-destructive below surface measurements of the sample.

A method for non-destructive x-ray diffraction includes emitting a first x-ray beam from an x-ray source with a first x-ray generating component based on a first desired measurement depth to measure a crystallographic signature of a sample at the first desired measurement depth, interchanging the first x-ray generating component with a second x-ray generating component to form a modified x-ray source, and emitting a second x-ray beam from the modified x-ray source based on a second desired measurement depth, wherein the second desired measurement depth is different from the first desired measurement depth, to non-destructively measure a crystallographic signature of the sample at the second desired depth.

The step of interchanging the first x-ray generating component with a second x-ray generating component can include interchanging a first x-ray target with a second x-ray target, and/or interchanging a first x-ray tube with a second x-ray tube.

It is contemplated that the method also includes adjusting the alignment of the sample relative to at least one of the x-ray source and the modified x-ray source to adjust an angle of incidence between the sample and at least one of the first x-ray beam and the second x-ray beam. The method can also include adjusting the alignment of a multi-axis sample stage relative to at least one of the x-ray source and the modified x-ray source, as described above.

These and other features of the systems and methods of the subject disclosure will become more readily apparent to those skilled in the art from the following detailed description of the embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, embodiments thereof will be described in detail herein below with reference to certain figures, wherein.

DETAILED DESCRIPTION OF THE EMBODIMENTS

Figure 1:
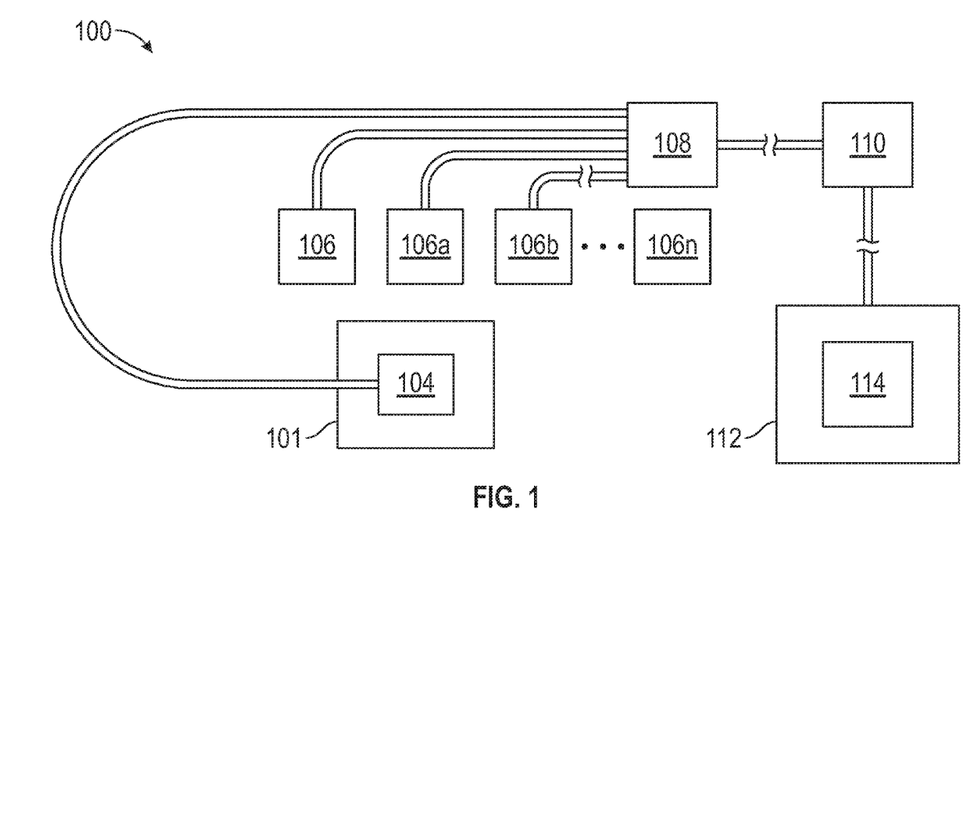
FIG. 1 is a schematic view of an exemplary embodiment of a non-destructive x-ray diffraction system constructed in accordance with the present disclosure, showing the interchangeable x-ray generating components and the sample.

Reference will now be made to the drawings wherein like reference numerals identify similar structural features or aspects of the subject disclosure. For purposes of explanation and illustration, and not limitation, a schematic top-elevation view of an exemplary embodiment of the x-ray diffraction system in accordance with the disclosure is shown in FIG. 1 and is designated generally by reference character 100. Other embodiments of x-ray diffraction systems in accordance with the disclosure, or aspects thereof, are provided in FIGS. 2-5, as will be described.

As shown in FIG. 1, an x-ray diffraction system 100 includes an x-ray source 102 having a first interchangeable x-ray generating component 104, a second interchangeable x-ray generating component 106, an actuator 108 and a controller 110 operatively connected to actuator 108. Second interchangeable x-ray generating component 106 is interchangeable with first interchangeable x-ray generating component 104. First interchangeable x-ray generating component 104 and second interchangeable x-ray generating component 106 allow x-ray source 102 to access different monochromatic x-ray energies within the same x-ray source 102.

Actuator 108 is operatively connected to both first interchangeable x-ray generating component 104 and second interchangeable x-ray generating component 106 for mechanically interchanging first interchangeable x-ray generating component 104 with second interchangeable x-ray generating component 106. It is contemplated that actuator 108 can be motorized and controlled by controller 110 through use of software, such as that described below. In addition, those skilled in the art will readily appreciate that actuator 108 can be automated and/or manually controlled.

Those skilled in the art will also readily appreciate that x-ray diffraction system 100 can include any suitable number of second interchangeable x-ray generating components 106 as indicated by additional second interchangeable x-ray generating components $106_a$, $106_b$ . . . and $106_n$. Any suitable second interchangeable x-ray generating components 106, $106_a$, $106_b$ . . . and/or $106_n$ can be interchanged with first interchangeable x-ray generating component 104. In addition, it is further contemplated that after interchanging first interchangeable x-ray generating component 104 with second interchangeable x-ray generating component 106, second interchangeable x-ray generating component 106 can be interchanged with an additional second interchangeable x-ray generating component, such as second interchangeable x-ray generating components $106_a$, $106_b$ . . . or $106_n$.

Those skilled in the art will readily appreciate that first interchangeable x-ray generating component 104 and second interchangeable x-ray generating component 106 can be interchangeable x-ray anode targets, e.g. interchangeable targets 204, 206, described below, or interchangeable x-ray tubes, e.g. interchangeable x-ray tubes 303, 305, 403, and 405, with respective anode targets, e.g. targets 304, 306, 404 and 406, within the respective tube. It is also contemplated that first interchangeable x-ray generating component 104 and second interchangeable x-ray generating components 106 can be mounted on the incident beam side of a sample stage, e.g. multi-axis sample stage 112, as described below. Those skilled in the art will also readily appreciate that an x-ray diffraction system 100, as described above and as shown in FIG. 1, can be used for non-destructive evaluation of residual stresses, such as those induced by peening or low plasticity burnishing, on an aerospace component, such as an aluminum fan blade, or other aluminum, titanium or nickel based aerospace components.

With continued reference to FIG. 1, x-ray diffraction system 100 includes a multi-axis sample stage 112 operatively connected to controller 110. Controller 110 is configured to adjust the alignment of multi-axis sample stage 112 relative to x-ray source 102 to adjust an angle of incidence between an x-ray beam emitted by x-ray source 102 and a sample 114 on multi-axis sample stage 112, based on a desired crystallographic measurement depth in sample 114. Those skilled in the art will readily appreciate that multi-axis sample stage 112 can be automated and/or manually adjusted.

Controller 110 is also configured to direct actuator 108 to interchange first interchangeable x-ray generating component 104 with second interchangeable x-ray generating component 106, after a first non-destructive below surface measurement is taken, based on a desired crystallographic measurement depth in sample 114 for a second non-destructive below surface measurement at a different depth. Those skilled in the art will readily appreciate that the interchangeable x-ray generating components 104 and 106 allow for multiple crystallographic measurements at a variety different depths within a single sample 114 without having to etch or machine off a surface of the sample 114. This tends to increase efficiency and reduce the cost of obtaining crystallographic measurements as compared with traditional x-ray diffraction systems and methods because the sample 114 can be used for its intended purpose after being evaluated.

Figure 2:
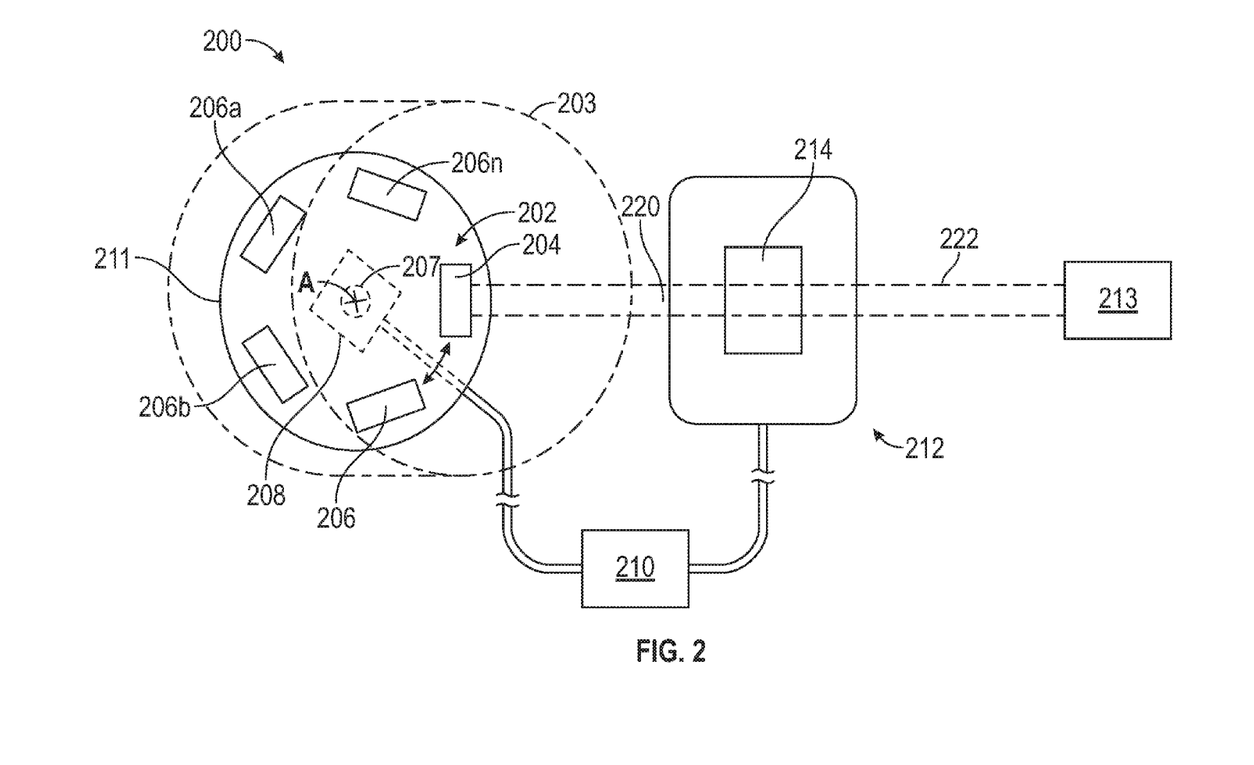
FIG. 2 is a schematic plan view of an exemplary embodiment of a non-destructive x-ray diffraction system constructed in accordance with the present disclosure, showing the interchangeable x-ray generating components as interchangeable x-ray targets that are mounted within an x-ray tube on a carousel.

Now with reference to FIG. 2, an x-ray diffraction system 200 is shown. X-ray diffraction system 200 is similar to x-ray diffraction system 100. In the case of x-ray diffraction system 200, the first interchangeable x-ray generating component is the first interchangeable x-ray target 204 and second interchangeable x-ray generating component is the second interchangeable x-ray target 206. X-ray diffraction system 200 also includes an x-ray source 202 having an x-ray tube 203 with a rotary carousel 211 disposed therein. First interchangeable x-ray target 204 and second interchangeable x-ray target 206 are interchangeably mounted on rotary carousel 211 within x-ray tube 203. Actuator 208 is operatively connected to rotary carousel 211 through a shaft 207 defining a shaft axis A mounted within x-ray tube 203. Actuator 208 operates to rotate shaft 207 about shaft axis A driving rotation of rotary carousel 211 about shaft axis A, as indicated by the double-headed arrow. The rotation of rotary carousel 211 operates to mechanically interchange first interchangeable x-ray target 204 with second interchangeable x-ray target 206.

Figure 3:
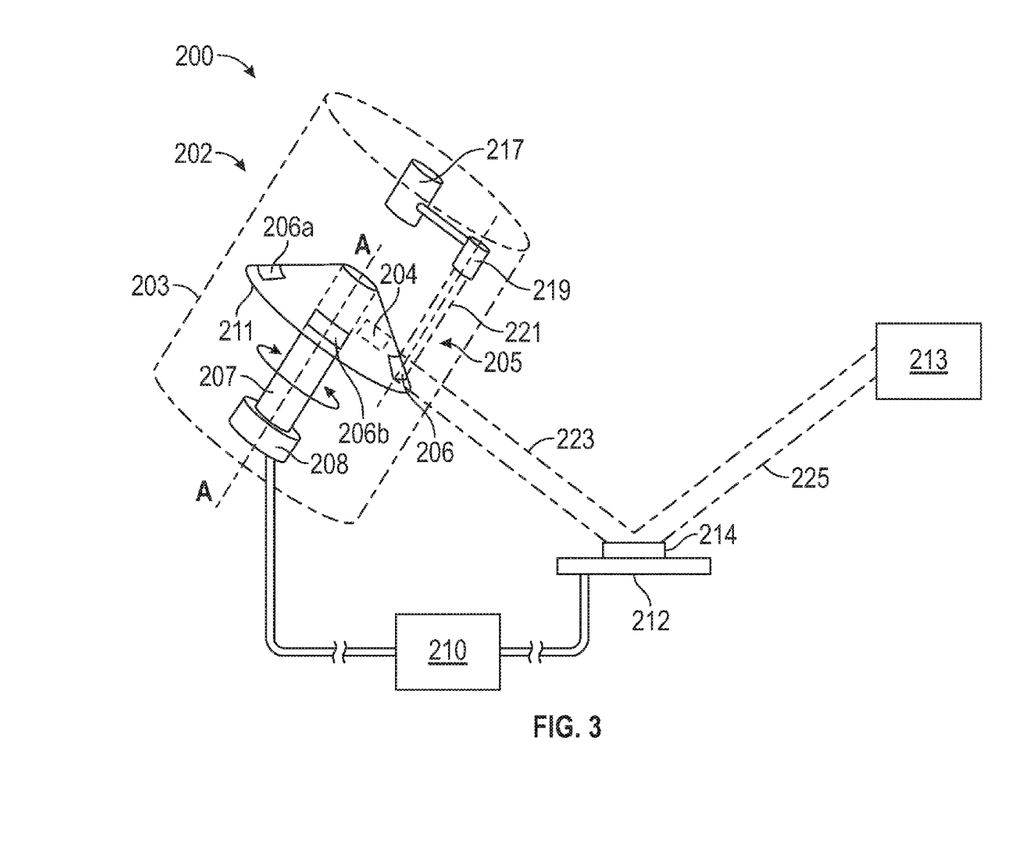
FIG. 3 is a schematic side view of the non-destructive x-ray diffraction system of FIG. 2, showing the actuator and shaft for rotating the carousel.

With continued reference to FIGS. 2 and 3, x-ray tube 203 includes a cathode 219 configured to emit a focused stream of accelerated electrons 221 directed at the first interchangeable x-ray target 204. Cathode 219 is held over rotary carousel 211 with a fixture 217. X-ray tube 203 and first interchangeable x-ray target 204 are configured to emit a first x-ray beam 220 at a first energy and first wavelength toward sample 214. A first diffracted beam 222 is then detected by a detector 213. After first x-ray beam 220 at a first energy and first wavelength is emitted and is detected, rotary carousel 211 is configured to be rotated about shaft axis A, as indicated by the double-headed arrow, to vertically align second interchangeable x-ray target 206 with cathode 219 in the path of the focused stream of accelerated electrons 221 forming a modified x-ray source 205, as shown in FIG. 3. The same x-ray tube 203 and second interchangeable x-ray target 206 are configured to emit a second x-ray beam 223 at a second energy and second wavelength toward sample 214. A second diffracted beam 225 is then detected by detector 213. Those skilled in the art will readily appreciate that each of the first diffracted beam 222 and second diffracted beam 225 results in detection of characteristics at different depths in a sample 214.

Those skilled in the art will readily appreciate that the first energy and/or the first wavelength of first x-ray beam 220 are different from the second energy and/or second wavelength of second x-ray beam 223 in order to penetrate to different depths in a sample 214. Those skilled in the art will readily appreciate that first and/or second interchangeable x-ray targets 204 and 206, respectively, can include chromium, vanadium, manganese, cobalt, copper, silver, molybdenum, titanium, and/or any other suitable target material.

Those skilled in the art will also readily appreciate that x-ray diffraction system 200 can include any suitable number of second interchangeable x-ray targets 206 to form an integrated system of anode targets within an x-ray tube 203, as indicated by additional second interchangeable x-ray targets $206_a$, $206_b$ . . . and $206_n$. Any suitable second interchangeable x-ray targets 206, $206_a$, $206_b$ . . . and/or $206_n$ can be interchanged with first interchangeable x-ray target 204 by manual or automatic rotation of rotary carousel 211. Those skilled in the art will readily appreciate that the double-headed arrows shown in FIGS. 2 and 3 indicate that rotary carousel 211 can be rotated in either direction depending on which second interchangeable x-ray target 206 is desired. In addition, it is further contemplated that after interchanging first interchangeable x-ray target 204 with second interchangeable x-ray target 206, second interchangeable x-ray target 206 can be interchanged with an additional second interchangeable x-ray target, such as second interchangeable x-ray targets $206_a$, $206_b$ . . . or $206_n$. While the carousel is shown herein as a rotary carousel 211, those skilled in the art will readily appreciate that x-ray diffraction system 200 can include a linear carousel, similar to linear carousel 311 shown in FIG. 4.

Figure 4:
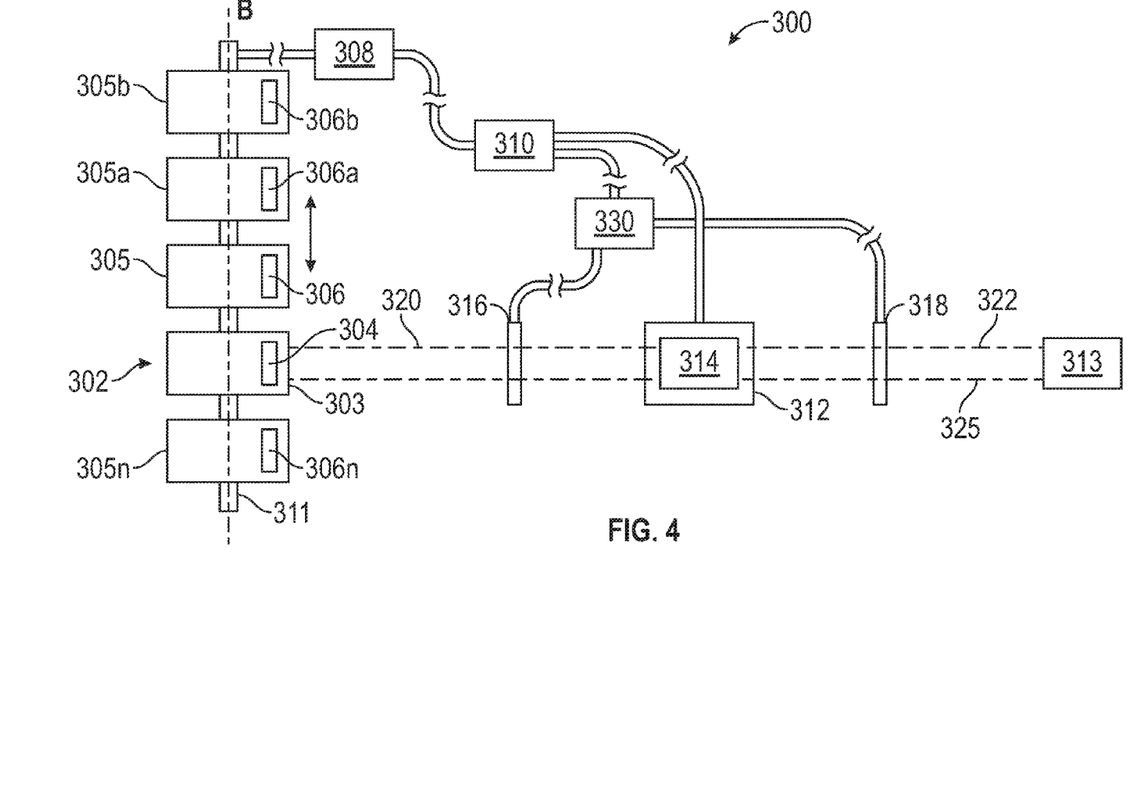
FIG. 4 is a schematic plan view of an exemplary embodiment of a non-destructive x-ray diffraction system constructed in accordance with the present disclosure, showing the interchangeable x-ray generating components as interchangeable x-ray tubes mounted on a linear carousel, each with a respective x-ray target.

As shown in FIG. 4, an x-ray diffraction system 300 is similar to x-ray diffraction system 100. In system x-ray diffraction 300, the first interchangeable x-ray generating component is the first interchangeable x-ray tube 303 and the second interchangeable x-ray generating component is the second interchangeable x-ray tube 305. First interchangeable x-ray tube 303 and second interchangeable x-ray tube 305 are mounted on a linear carousel 311. Actuator 308 is operatively connected to linear carousel 311. Actuator 308 operates to move linear carousel 311 along carousel axis B, as indicated by the double-headed arrow. The movement of linear carousel 311 operates to mechanically interchange first interchangeable x-ray tube 303 with second interchangeable x-ray tube 305. First interchangeable x-ray tube 303 is configured to emit a first x-ray beam 320 at a first energy and first wavelength. After first x-ray beam 320 at a first energy and first wavelength is emitted, linear carousel 311 is configured to move second interchangeable x-ray tube 305 downward along carousel axis B, as oriented in FIG. 4, to align with sample 314. Second interchangeable x-ray tube 305 is configured to emit a respective second x-ray beam at a second energy and second wavelength. First diffracted x-ray beam 322 and second diffracted x-ray beam 325 are similar to those x-ray beams described above with respect to first and second interchangeable x-ray targets 204 and 206, respectively. The first diffracted x-ray beam 322 and second diffracted x-ray beam 325 detected by a detector 313 similar to those x-ray beams described above with respect to first interchangeable x-ray target 204 and second interchangeable x-ray target 206, respectively.

With continued reference to FIG. 4, first interchangeable x-ray tube 303 and second interchangeable x-ray tube 305 each include a respective x-ray target 304 and 306. Those skilled in the art will readily appreciate that x-ray target 304 of first interchangeable x-ray tube 303 can be different from x-ray target 306 of second interchangeable x-ray tube 305 in order to achieve the different wavelengths and energies described above. Those skilled in the art will readily appreciate that respective x-ray targets 304 and 306 of the first and second interchangeable x-ray tubes 303 and 305, respectively, can each include a different material as described above.

Those skilled in the art will also readily appreciate that x-ray diffraction system 300 can include any suitable number of second interchangeable x-ray tubes 305 with respective x-ray targets 306 as indicated by additional second interchangeable x-ray tubes $305_a$, $305_b$ . . . and $305_n$ and respective x-ray targets $306_a$, $306_b$ . . . and $306_n$. It is contemplated that x-ray targets 306, $306_a$, $306_b$ . . . and $306_n$ can each include a different material as described above. Any suitable second interchangeable x-ray tubes 305, $305_a$, $305_b$ . . . and/or $305_n$ can be interchanged with first interchangeable x-ray tube 303 by manual or automatic actuation of linear carousel 311. Those skilled in the art will readily appreciate that the double-headed arrow shown in FIG. 4 indicates that linear carousel 311 can be moved along carousel axis B in either direction depending on which second interchangeable x-ray tube 305 is desired. In addition, it is further contemplated that after interchanging first interchangeable x-ray tube 303 with second interchangeable x-ray tube 305, second interchangeable x-ray tube 305 can be interchanged with an additional second interchangeable x-ray tube, such as second interchangeable x-ray tubes $305_a$, $305_b$ . . . or $305_n$.

Figure 5:
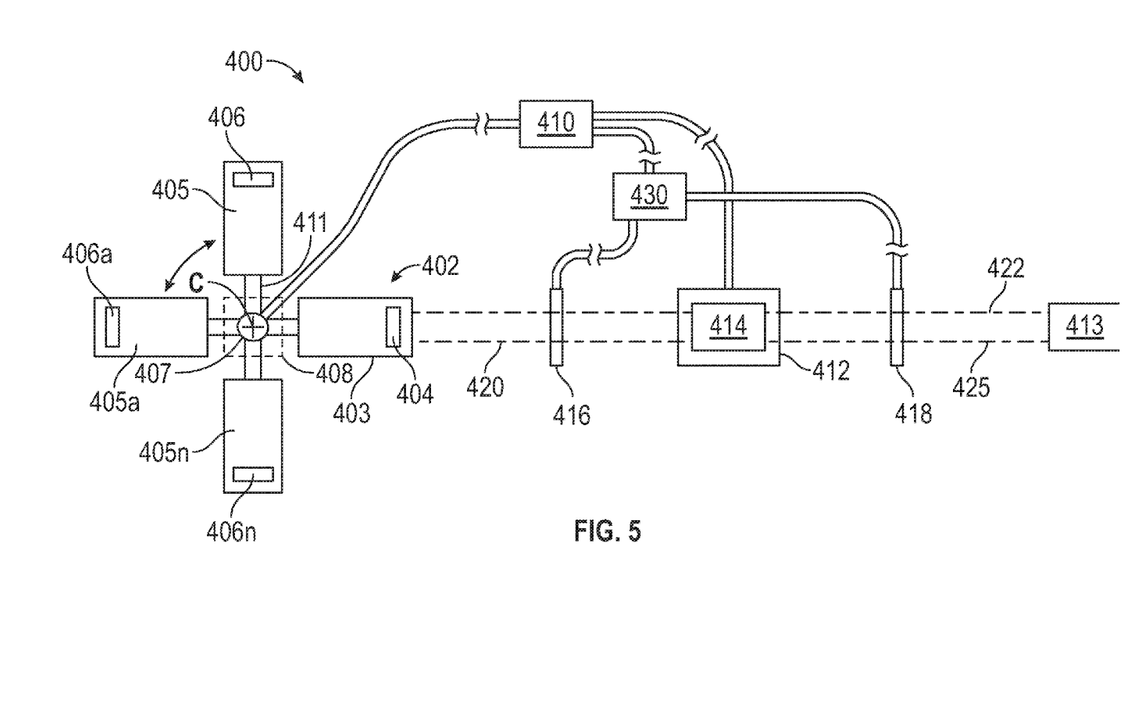
FIG. 5 is a schematic plan view of an exemplary embodiment of a non-destructive x-ray diffraction system constructed in accordance with the present disclosure, showing the interchangeable x-ray generating components as interchangeable x-ray tubes mounted to a rotary carousel, each with a respective x-ray target.

Now with reference to FIG. 5, an x-ray diffraction system 400 is shown. X-ray diffraction system 400 is similar to x-ray diffraction system 100. In x-ray diffraction system 400, the first interchangeable x-ray generating component is the first interchangeable x-ray tube 403 and the second interchangeable x-ray generating component is the second interchangeable x-ray tube 405 similar to x-ray diffraction system 300. In x-ray diffraction system 400, the carousel is a rotary carousel 411. First interchangeable x-ray tube 403 and second interchangeable x-ray tube 405 are mounted on rotary carousel 411. Actuator 408 is operatively connected to rotary carousel 411 through a shaft 407 defining a shaft axis C. Actuator 408 operates to rotate shaft 407 about shaft axis C driving rotation of rotary carousel 411 about shaft axis C, as indicated by the double-headed arrow. The rotation of rotary carousel 411 operates to mechanically interchange first interchangeable x-ray tube 403 with second interchangeable x-ray tube 405. First interchangeable x-ray tube 403 and second interchangeable x-ray tube 405 each include a respective x-ray target 404 and 406, similar to x-ray targets 304 and 306, described above.

With continued reference to FIG. 5, first interchangeable x-ray tube 403 and its respective x-ray target 404 are configured to emit a first x-ray beam 420 at a first energy and first wavelength. After first x-ray beam 420 at a first energy and first wavelength is emitted, rotary carousel 411 is configured to be rotated about shaft axis C to horizontally align second interchangeable x-ray tube 405 with sample 414. Second interchangeable x-ray tube 405 is configured to emit a respective second x-ray beam at a second energy and second wavelength. First diffracted x-ray beam 422 and second diffracted x-ray beam 425 are similar to those x-ray beams described above with respect to first interchangeable x-ray target 204 and second interchangeable x-ray target 206, respectively. The first diffracted x-ray beam 422 and second diffracted x-ray beam 425 are detected by a detector 413 similar to those x-ray beams described above with respect to first interchangeable x-ray target 204 and second interchangeable x-ray target 206, respectively.

Those skilled in the art will also readily appreciate that second interchangeable x-ray tubes $405_a$- . . . -$405_n$ are similar to second interchangeable x-ray tubes $305_a$, $305_b$ . . . and $305_n$ described above. The x-ray diffraction system 400 can include any suitable number of second interchangeable x-ray tubes 405 with respective x-ray targets 406 as indicated by additional second interchangeable x-ray tubes $405_a$ . . . $405n$ and respective x-ray targets $406_a$ . . . $406_n$. Any suitable second interchangeable x-ray tubes 405, $405_a$ . . . and/or $405_n$ can be interchanged with first interchangeable x-ray tube 403 by manual or automatic rotation of rotary carousel 411. Those skilled in the art will readily appreciate that the double-headed arrow shown in FIG. 5 indicates that rotary carousel 411 can be rotated about shaft axis C in either direction depending on which second interchangeable x-ray tube 405 is desired. Those skilled in the art will also readily appreciate that while linear and rotary carousels are described herein, first interchangeable x-ray generating component and second interchangeable x-ray generating component, whether x-ray tubes, targets or both, can be operatively connected to any other suitable automatic or manual interchanging device.

With reference to FIGS. 1-5, it is contemplated that x-ray diffraction systems, e.g. x-ray diffraction systems 100, 200, 300 and 400 can include incident beam collimating optics 316 and 416 and diffracted beam collimating optics 318 and 418, which allow spot size selection based on target, collimation and angle of incidence. An actuator, e.g. actuator 330 and 430, is operatively connected to incident beam collimating optics 316 and 416 and diffracted beam collimating optics 318 and 418, respectively, and is controlled by a controller, e.g. controller 110, 210, 310 and 410, to mechanically change incident beam collimating optics 316 and 416 and diffracted beam collimating optics 318 and 418 through use of software, as described below. Incident beam collimating optics 316 and 416 and diffracted beam collimating optics 318 and 418, can be mounted to carousels, similar to those described above, or operatively connected to any other suitable automatic or manual interchanging device. Those skilled in the art will readily appreciate that while incident beam collimating optics 316 and 416, diffracted beam collimating optics 318 and 418, and actuators 330 and 430 are shown and described herein with respect to FIGS. 4 and 5, incident beam collimating optics 316 and 416 and diffracted beam collimating optics 318 and 418 and their actuators 330, 430 can be included in any of the embodiments described herein.

With reference now to FIGS. 1-5, a tangible, non-transitory, computer-readable media (e.g., disks/CDs/RAM/EEPROM/etc.) having software encoded thereon, is described. The software, when executed by a processor, e.g. controller 110, 210,310, and 410, is operable to receive a desired crystallographic measurement depth of a sample, e.g. samples 114, 214, 314, and 414, select an x-ray target, e.g. interchangeable x-ray targets 206, 306 and 406, incident beam collimating optic, e.g. incident beam collimating optics 316 and 416, and diffracted beam collimating optic, e.g. diffracted beam collimating optics 318 and 418, for use in non-destructive x-ray crystallography, based on the desired crystallographic measurement depth.

The software, when executed by the processor is further operable to execute a command to cause an actuator, e.g. actuator 108, 208, 308, 408, 330 and 430, to mechanically alter at least one of a current x-ray target, an incident beam collimating optic, and a diffracted beam collimating optic, to match the selected x-ray target, incident beam collimating optic and diffracted beam collimating optic for non-destructive below surface measurements of the sample. Those skilled in the art will readily appreciate that the actuator can be automated and/or manually controlled to perform the mechanical alteration described above.

With further reference to FIGS. 1-5, a method for non-destructive x-ray diffraction includes emitting a first x-ray beam, e.g. first x-ray beams 220, 320 and 420, from an x-ray source, e.g. x-ray sources 102, 202, 302, and 402, with a first interchangeable x-ray generating component, e.g. first interchangeable x-ray generating components 104, 204, 303, and 403, based on a first desired measurement depth to measure a crystallographic signature of a sample, e.g. sample 114, 214, 314 and 414, at the first desired measurement depth, interchanging the first interchangeable x-ray generating component with a second interchangeable x-ray generating component, e.g. second interchangeable x-ray generating components 106, 206, 305, and 405, to form a modified x-ray source, e.g. modified x-ray source 205, with the second interchangeable x-ray generating components instead of the first interchangeable x-ray generating components, and emitting a second x-ray beam, e.g. second x-ray beam 223, from the modified x-ray source based on a second desired measurement depth, wherein the second desired measurement depth is different from the first desired measurement depth, to non-destructively measure a crystallographic signature of the sample at the second desired depth. Those skilled in the art will readily appreciate that by first and second x-ray beams having differences in wavelength and/or energy characteristics, as described above, this method avoids having to etch or machine off a layer of the sample to obtain a crystallographic measurement at a different depth.

With continued reference to FIGS. 1-5, those skilled in the art will readily appreciate that the method can also include adjusting the alignment of the sample relative to at least one of the x-ray source and the modified x-ray source to adjust an angle of incidence between at least one of the first x-ray beam, second x-ray beam, and the sample. It is further contemplated that the method can also include adjusting the alignment of a multi-axis sample stage, e.g. multi-axis sample stages 112, 212, 312, and 412, relative to at least one of the x-ray source and the modified x-ray source, as described above. Those skilled in the art will readily appreciate that step of interchanging the first interchangeable x-ray generating component with the second interchangeable x-ray generating component can include interchanging the first interchangeable x-ray generating component with the second interchangeable x-ray generating component manually and/or automatically, for example, by using an automated actuator and/or a manually controlled actuator.

While shown and described herein as having only first and second interchangeable x-ray generating components those skilled in the art will readily appreciate that a single x-ray diffraction system, can include more than two interchangeable components in order to provide a variety of wavelength and energy options depending on the desired crystallographic measurement depth in a certain sample.

The methods and systems described above and shown in the drawings, provide for superior properties including improved efficiency and reduced cost. It should be recognized that these embodiments are merely illustrative of the principles of the present invention. Numerous modifications and adaptations thereof will be readily apparent to those skilled in the art without departing from the spirit and scope of the invention.

What is claimed is:

1. An x-ray diffraction system comprising:
    an x-ray source including a first interchangeable x-ray generating component;
    a second interchangeable x-ray generating component configured to be interchanged with the first interchangeable x-ray generating component;
    an actuator operatively connected to both the first interchangeable x-ray generating component and the second interchangeable x-ray generating component for mechanically interchanging the first interchangeable x-ray generating component with the second interchangeable x-ray generating component; and
    a controller operatively connected to the actuator,
    wherein the first interchangeable x-ray generating component comprises a first interchangeable x-ray tube and the second interchangeable x-ray generating component comprises a second interchangeable x-ray tube.

2. An x-ray diffraction system as recited in claim 1, wherein the first interchangeable x-ray tube is configured to emit a respective first x-ray beam at a first energy and a first wavelength and wherein the second interchangeable x-ray tube is configured to emit a respective second x-ray beam at a second energy and a second wavelength, wherein at least one of the first energy and the first wavelength is different from at least one of the second energy and the second wavelength.

3. An x-ray diffraction system as recited in claim 1, wherein the first interchangeable x-ray tube includes a first interchangeable x-ray target and the second interchangeable x-ray tube includes a second interchangeable x-ray target, wherein the first interchangeable x-ray target of the first interchangeable x-ray tube is different from the second interchangeable x-ray target of the second interchangeable x-ray tube.

4. An x-ray diffraction system as recited in claim 3, wherein at least one of the first interchangeable x-ray target of the first interchangeable x-ray tube and the second interchangeable x-ray target of the second interchangeable x-ray tube includes a material selected from the group consisting of copper, silver, chromium, vanadium, manganese, cobalt, molybdenum, and titanium.

5. A method for non-destructive x-ray diffraction, comprising:
    emitting a first x-ray beam from an x-ray source with a first interchangeable x-ray generating component based on a first desired measurement depth, wherein the first x-ray beam has first energy and a first wavelength, wherein the first x-ray beam is emitted in response to a first focused stream of electrons directed at the first interchangeable x-ray generating component and wherein the first x-ray beam is not parallel to the first focused stream of electrons, wherein the first x-ray beam is not a transmitted x-ray beam;
    measuring a crystallographic signature of a sample at the first desired measurement depth;
    interchanging the first interchangeable x-ray generating component with a second interchangeable x-ray generating component to form a modified x-ray source;
    emitting a second x-ray beam from the modified x-ray source based on a second desired measurement depth, wherein the second desired measurement depth is different from the first desired measurement depth, wherein the second x-ray beam has second energy and a second wavelength, wherein the second x-ray beam is emitted in response to a second focused stream of electrons directed at the second interchangeable x-ray generating component and wherein the second x-ray beam is not parallel to the second focused stream of electrons, wherein the second x-ray beam is not a transmitted x-ray beam; and measuring a crystallographic signature of the sample at the second desired measurement depth.

6. A method as recited in claim 5, wherein the step of interchanging the first interchangeable x-ray generating component with a second interchangeable x-ray generating component includes interchanging a first interchangeable x-ray target with a second interchangeable x-ray target.

7. A method as recited in claim 5, wherein at least one of the first energy and the first wavelength is different from at least one of the second energy and the second wavelength.

8. A method as recited in claim 5, further comprising adjusting an alignment of the sample relative to at least one of the x-ray source and the modified x-ray source to adjust an angle of incidence between at least one of the first x-ray beam, the second x-ray beam, and the sample.

9. A method as recited in claim 5, further comprising adjusting an alignment of a multi-axis sample stage relative to at least one of the x-ray source and the modified x-ray source based on a desired crystallographic measurement depth in the sample.

10. A method for non-destructive x-ray diffraction, comprising:

emitting a first x-ray beam from an x-ray source with a first interchangeable x-ray generating component based on a first desired measurement depth;

measuring a crystallographic signature of a sample at the first desired measurement depth;

interchanging the first interchangeable x-ray generating component with a second interchangeable x-ray generating component to form a modified x-ray source;

emitting a second x-ray beam from the modified x-ray source based on a second desired measurement depth, wherein the second desired measurement depth is different from the first desired measurement depth; and measuring a crystallographic signature of the sample at the second desired measurement depth, wherein the step of interchanging the first interchangeable x-ray generating component with a second interchangeable x-ray generating component includes interchanging a first interchangeable x-ray tube with a second interchangeable x-ray tube.

11. A tangible, non-transitory, computer-readable media having software encoded thereon, the software, when executed by a processor, operable to:

receive a first desired crystallographic measurement depth of a sample;

select a first interchangeable x-ray target and at least one of an incident beam collimating optic and a diffracted beam collimating optic based on the first desired crystallographic measurement depth for use in non-destructive x-ray crystallography, wherein the first interchangeable x-ray target is configured to emit a first x-ray beam at a first energy and a first wave length towards the sample, wherein the first x-ray beam is emitted in response to a first focused stream of electrons directed at the first interchangeable x-ray generating component and wherein the first x-ray beam is not parallel to the first focused stream of electrons, wherein the first x-ray beam is not a transmitted x-ray beam;

execute a command to cause an actuator to mechanically alter the current interchangeable x-ray target and at least one of the incident beam collimating optic and the diffracted beam collimating optic to match the selected first interchangeable x-ray target and at least one of the incident beam collimating optic and the diffracted beam collimating optic for non-destructive below surface measurements of the sample;

receive a second desired crystallographic measurement depth of the sample;

select a second interchangeable x-ray target and at least one of the incident beam collimating optic and the diffracted beam collimating optic based on the second desired crystallographic measurement depth for use in non-destructive x-ray crystallography, wherein the second interchangeable x-ray target is configured to emit a second x-ray beam at a second energy and a second wave length towards the sample, wherein the second x-ray beam is emitted in response to a second focused stream of electrons directed at the second interchangeable x-ray generating component and wherein the second x-ray beam is not parallel to the second focused stream of electrons, wherein the second x-ray beam is not a transmitted x-ray beam; and execute a command to cause an actuator to mechanically alter the current interchangeable x-ray target and at least one of the incident beam collimating optic and the diffracted beam collimating optic to match the selected second interchangeable x-ray target and at least one of the incident beam collimating optic and the diffracted beam collimating optic for non-destructive below surface measurements of the sample.

* * * * *